United States Patent [19]

Chernowsky et al.

[11] Patent Number: 4,751,075

[45] Date of Patent: Jun. 14, 1988

[54] ANHYDROUS COSMETIC COMPOSITIONS FOR THERMAL SKIN TREATMENTS

[75] Inventors: Eugene N. Chernowsky, Woodland Hills; Michael G. Ng, Northridge, both of Calif.

[73] Assignee: Redken Laboratories, Inc., Canoga Park, Calif.

[21] Appl. No.: 817,002

[22] Filed: Jan. 8, 1986

[51] Int. Cl.[4] .............................. A61K 7/48; A61K 9.07
[52] U.S. Cl. ......................................... 424/83; 424/59; 514/458; 514/474; 514/725; 514/773; 514/783; 514/784; 514/785; 514/873; 514/904; 514/969
[58] Field of Search ............... 514/843, 969, 846, 773; 424/83, 59

[56] References Cited

U.S. PATENT DOCUMENTS

| | | | |
|---|---|---|---|
| 2,982,691 | 5/1961 | Winsten | 424/83 |
| 3,029,188 | 4/1962 | Cyr et al. | 424/83 |
| 3,079,299 | 2/1963 | Heilig | 424/83 |
| 3,215,599 | 11/1965 | Thau et al. | 424/83 |
| 4,272,544 | 6/1981 | Cella et al. | 424/83 |
| 4,372,944 | 2/1983 | Herrold | 424/83 |
| 4,454,113 | 6/1984 | Hemker | 424/63 |

FOREIGN PATENT DOCUMENTS

| | | | |
|---|---|---|---|
| 0132631 | 2/1985 | European Pat. Off. | 424/63 |
| 0064128 | 4/1983 | Japan | 514/969 |
| 0144715 | 8/1984 | Japan | 514/969 |
| 1503444 | 3/1978 | United Kingdom | 424/83 |

OTHER PUBLICATIONS

The Extra Pharmacopoeia, 26th Edition, 1972, p. 1274, col. 2.
The Pharmaceutical Codex, 11th Edition, 1979, pp. 612–613.

*Primary Examiner*—Dale R. Ore
*Attorney, Agent, or Firm*—Christie, Parker & Hale

[57] ABSTRACT

The invention comprises compositions for cosmetic skin treatment utilizing the application of heat to the skin. The compositions include between 30 and 70 percent by weight of petrolatum, between 20 and 68 percent by weight of triglycerides, preferably capric, caprylic and stearic triglycerides, and between 0.1 and 5 percent by weight of polyethylene.

6 Claims, No Drawings

4,751,075

ANHYDROUS COSMETIC COMPOSITIONS FOR THERMAL SKIN TREATMENTS

FIELD OF THE INVENTION

This invention relates to compositions for cosmetic skin treatment utilizing the application of heat.

BACKGROUND OF THE INVENTION

The cosmetic treatment of the skin often combines the use of cosmetic preparations with the application of heat. The use of heat provides a number of benefits. It stimulates circulation; it increases the liquidity of the cosmetic preparation, improving its penetration into the skin; it reduces skin stiffness.

Heat may be applied to the skin in a number of ways. The cosmetic preparation itself may be warmed above ambient temperature before being applied to the skin and allowed to cool. Melted paraffin preparations are an example of this technique. Alternatively, the cosmetic preparation is applied to the skin at ambient temperature and hot compresses are applied over the preparation, or the skin is manipulated by means of facial irons or other externally heated sources. A further step in the treatment may involve massage of the warm cosmetic composition on and into the skin surface.

An important part of such treatment is the cosmetic preparation itself. It must possess a number of qualities. The composition must be sufficiently stable that heat does not cause breakdown of ingredients to a non-homogeneous state, yet sufficiently liquid to spread easily under ambient temperature. The composition should readily transport warmth to the skin without requiring extended periods of heating to achieve elevated skin temperature. It should not react to cool the skin below body temperature upon application, thus minimizing the effect of external heat. Its frictional characteristic should not increase upon warming, since this would hamper the ease of manipulation necessary to a massage.

Cosmetic compositions that have been used for thermal treatment of the skin include paraffin, candellila, or ozokerite, carnauba, and other waxes used to formulate "wax masks" which are applied to the skin in a warm liquid state and allowed to cool. However, the pure waxes or wax blends tend to have high frictional effects on the skin. Moreover, they must be premelted and applied while warm. They rapidly cool and set at ambient temperature, allowing no time for manipulation of the skin while the mask is hot.

SUMMARY OF THE INVENTION

The present invention comprises anhydrous cosmetic compositions that spread easily on the skin at ambient temperatures and warm the skin prior to the application of external heat. When heat is applied, the compositions enable manipulation of the skin with heat devices without any accompanying increase in frictional effects.

The compositions are substantially anhydrous and comprise petrolatum, at least one triglyceride, and polyethylene. Preferably, the triglycerides include a mixture of capric, caprylic and stearaic triglycerides. The petrolatum and the triglycerides form about 90 percent to 98 percent by weight of the composition, the petrolatum comprising about 30 to about 70 percent by weight of the composition, and the triglycerides comprising about 20 to about 68 percent of the composition.

The composition may also include about one percent of other ingredients, such as active ingredients for skin treatment. Active ingredients include oil-soluble vitamins, active fatty acids, anti-irritants, oil-soluble protein derivatives, and phospholipids. Small quantities of other ingredients such as preservatives, fragrance, oil-soluble color, oils, esters hydrocarbons, and waxes can be incorporated into the basic composition. The presence of these other ingredients is not essential to the invention.

The compositions can be applied to the skin in a number of ways. The compositions can be prewarmed and then applied to the skin. Alternatively, the compositions can be applied to the skin and hot compresses applied over the composition, or the skin can be manipulated with heated devices such as facial irons.

DETAILED DESCRIPTION

The invention relates to anhydrous cosmetic compositions comprising, (1) petrolatum; (2) triglycerides; and (3) polyethylene.

The petrolatum and triglycerides form the bulk of the composition, about 90 to 98 percent by weight of the composition. (All percentages in this application are given in terms of weight.) The petrolatum warms the skin through occlusion and increases the moisture content of the stratum corneum of the skin. It also tends to plasticize the composition, making it easier to scoop up the desired amount directly with the fingers rather than using a spatula or other implement. The petrolatum, also known as petroleum jelly, has been previously used in massage. However, used by itself it has several undesirable characteristics. It is unctuous and has a high coefficient of friction. The triglycerides reduce the greasiness of the petrolatum.

The relative amounts of petrolatum and triglycerides present depend on the consistency and "feel" of the composition desired. Preferably, the petrolatum should range between the amount of about 30 percent and about 70 percent of the composition. If the composition contains less than about 30 percent of the petrolatum, it tends to be too solid and insufficiently plastic for easy use. If the composition contains more than about 70 percent of petrolatum, it tends to be greasy. The presently preferred composition contains 42 percent petrolatum.

The composition preferably contains about 20 percent to about 68 percent triglycerides. The presently preferred triglycerides are capric, caprylic and stearic triglycerides. These triglycerides are desirable because they are odorless and they enable the composition to be free of perfume, which can act as an irritant. The three triglycerides also impart a drier, more desirable "feel" to the composition. Finally, they have low viscosity and are especially effective solubilizing various cosmetic skin treatment incredients that may be added to the composition. Stearic triglyceride is solid and tends to render the composition more solid; capric acid and caprylic triglycerides are liquid. Preferably, a mixture of all three triglycerides is used. The relative proportions depend on the desired hardness of the composition. Other triglycerides may be added or substituted, especially if an odorless composition is not required. The presently preferred composition contains a mixture of capric, caprylic and stearic triglycerides.

The composition further contains about 0.1 to about 5 percent of polyethylene. A preferred range is about 1 percent to about 3 percent; the presently preferred composition contains 1 percent polyethylene. The polyethylene increases the melting point and setting point of the preparation to keep it firm at ambient temperature, yet spreadable. It is important that the composition not have too low a melting point since it may be stored at high temperatures before use. If the composition melts and it is not stored on a level surface, when the temperature cools the composition resets in a different position and may even adhere to the lid.

If the composition contains less than 0.1 percent polyethylene, there is little effect on the melting point. If the composition contains more than 3 percent polyethylene, it tends to harden; if there is more than 5 percent polyethylene, it becomes undesirably hard. Preferably, the polyethylene should be chosen from polyethylenes with a relatively low melting point, for instance between about 85° C. and about 100° C.

The composition may also include other ingredients, such as active ingredients for cosmetic treatment of the skin. The active ingredients should be oil-soluble. The active ingredients can be customized for skin type and condition. Active ingredients for skin treatment include, but are not limited to, oil-soluble vitamins such as retinyl palmitate, tocopherol, and ascorbyl palmitate; active fatty acids such as gamma linolenic; anti-irritants such as bisabolol; as well as oil-soluble protein derivatives, shikonin, guaiazulene, primrose oil, undecylenates and phospholipids. Small quantities of other ingredients can also be incorporated into the basic composition. These may includes oils, esters, hydrocarbons, and waxes. Finally, the compositions may include preservatives, fragrance or oil-soluble color. Compositions containing only capric, caprylic and stearic triglycerides are relatively odorless, and fragrance can be dispensed with. This renders the composition particularly suitable for persons with sensitive skin, since fragrance can contribute to skin irritation. If other triglycerides are used, fragrance may be needed if the odor is objectionable.

Since the compositions are substantially anhydrous, no emulsifiers need be added. Preservatives can be kept to a minimum level. Water contributes to degradation of the composition which is counteracted by the addition of preservatives. Emulsifiers and preservatives may act as irritants to the skin.

The absence of water results in other advantages. The anhydrous compositions are occlusive to the skin and thus increase the moisture content of the skin's stratum corneum, improving the softness and flexibility of the skin. Unlike an emulsive composition, an anhydrous composition can be a single phase homogeneous system whose components do not separate upon warming. Since there is no water, the compositions are fully active with respect to emollients and lubricants needed for massage. Finally, water-insoluble emollients and lubricants do not increase in friction during massage through water evaporation.

To make the composition, the petrolatum, triglycerides and polyethylene are combined in a mixing vessel provided with a source of heat. The ingredients are mixed constantly as the temperature is raised to 3° C. above the melting point of the highest melting ingredient. For example, for polyethylene with a melting point of 86° C., the ingredients are brought to a temperature of 89° C. and held at that temperature until the batch is clear. The stage at which other ingredients are added depends upon the tolerance to heat of the particular ingredient. The composition is filled into jars at approximately 55°-60° C., which is the lowest temperature at which it remains clear. The filled jars are allowed to cool until the composition has solidified; then they are capped.

It has been found that small quantities such as 0.06 ounces (2 grams) are sufficient for a facial treatment. The compositions can be used along with the heat treatment in a number of ways. The composition may be prewarmed before it is applied to the skin. Alternatively, the composition is first applied to the skin and hot compresses are applied over it. The composition can be applied to the skin which is then manipulated with external heated devices, such as facial irons. This method combines the benefits of massage and heat, and takes full advantage of the suitability of the composition for both massage and the application of heat.

The preceding description has been presented with reference to the currently preferred embodiment of the invention. Persons skilled in the art and technology to which this invention pertains will appreciate that variations can be made without departing from the essence and scope of the invention.

What is claimed is:

1. A substantially anhydrous composition for thermal treatment of the skin, comprising petrolatum, at least one triglyceride, and polyethylene, where the petrolatum and triglycerides comprise about 90 percent to about 98 percent by weight of the composition, and polyethylene comprises about 0.1 percent to about 5 percent by weight of the composition.

2. A composition as claimed in claim 1, where petrolatum comprises between about 30 percent to about 70 percent by weight of the composition, and triglycerides comprise between about 20 percent and about 68 percent by weight of the composition.

3. A composition as claimed in claim 1, where the triglyceride is selected from the group consisting of capric, caprylic and stearic triglycerides, and mixtures thereof.

4. A composition as claimed in claim 1, where the triglyceride is present as a mixture of capric, caprylic and stearic triglycerides.

5. A composition as claimed in claim 1, further comprising at least one ingredient selected from the group consisting of oil-soluble vitamins, fatty acids, anti-irritants, oil-soluble protein derivatives, shikonin, guaiazulene, primrose oil, undecylenates, and phospholipids.

6. A substantially anhydrous composition for thermal treatment of the skin, comprising about 42 percent by weight of petrolatum, about 56 percent by weight of a mixture of capric, caprylic and stearic triglycerides, about one percent by weight of polyethylene, and about one percent by weight of other ingredients selected from the group consisting of oils, esters, waxes, fragrances, preservatives and oil soluble color.

* * * * *